(12) United States Patent
Chiarin et al.

(10) Patent No.: US 8,119,082 B2
(45) Date of Patent: Feb. 21, 2012

(54) PLASTIC TEST TUBE FOR TAKING BLOOD SAMPLES

(75) Inventors: Renzo Chiarin, Arzergrande (IT); Ulisse Chiarin, Arzergrande (IT)

(73) Assignee: Vacutest Kima S.r.l., Arzergrande, Padua (IT)

( * ) Notice: Subject to any disclaimer, the term of this patent is extended or adjusted under 35 U.S.C. 154(b) by 429 days.

(21) Appl. No.: 12/095,536

(22) PCT Filed: Dec. 6, 2006

(86) PCT No.: PCT/IB2006/003589
§ 371 (c)(1),
(2), (4) Date: Oct. 3, 2008

(87) PCT Pub. No.: WO2007/072144
PCT Pub. Date: Jun. 28, 2007

(65) Prior Publication Data
US 2010/0254859 A1    Oct. 7, 2010

(30) Foreign Application Priority Data
Dec. 19, 2005   (IT) .............. PD2005A0372

(51) Int. Cl.
*B01L 3/14*    (2006.01)
(52) U.S. Cl. ....... 422/549; 422/68.1; 422/913; 422/914; 428/36.7; 428/36.91; 428/446; 428/448; 428/500

(58) Field of Classification Search .......... 428/36.7, 428/36.91, 446, 448, 500, 702, 413, 480; 422/68.1, 100, 101, 102, 103, 913, 914, 549, 422/554, 555, 556, 557, 558
See application file for complete search history.

(56) References Cited

U.S. PATENT DOCUMENTS

| 4,856,533 | A | * | 8/1989 | Anraku et al. | 600/576 |
| 5,326,534 | A | | 7/1994 | Yamazaki et al. | |
| 5,952,069 | A | * | 9/1999 | Tropsha et al. | 428/36.7 |

FOREIGN PATENT DOCUMENTS

| EP | 164583 | 12/1985 |
| EP | 571116 | 11/1993 |
| EP | 603717 | 6/1994 |
| EP | 735921 | 10/1996 |
| EP | 1175941 | 1/2002 |

* cited by examiner

*Primary Examiner* — In Suk Bullock
*Assistant Examiner* — Sharon Pregler
(74) *Attorney, Agent, or Firm* — Shoemaker and Mattare

(57) ABSTRACT

Plastic test tube for taking blood samples, comprising a hollow tubular body and an adhesive protective film able to adhere to the tubular body. The tubular body is made of polyethylene terephthalate and has: a tubular wall which delimits a working volume and defines an outer surface; an open mouth for insertion of liquids at a first end of the wall; and a bottom for closing a second end of the wall. The adhesive protective film is able to adhere to the wall of the tubular body over at least a portion of the outer surface. The test tube is characterized in that the wall of the tubular body has a thickness in the range of 1 to 3 mm and in that the protective film is defined by a layer of polypropylene, polyethylene or copolymers thereof. The layer has a thickness in the range of between 40 and 60 μm and is able to form a liquid barrier.

10 Claims, 4 Drawing Sheets

| t | $V_1$ (ml) | $\delta V_1$ | $V_2$ (ml) | $\delta V_2$ | $V_1/V_2$ |
|---|---|---|---|---|---|
| 0 | 0.44 | +10% | 3.68 | +2.2% | 0.121 |
| 1 | 0.426 | +6.5% | 3.65 | +1.4% | 0.117 |
| 2 | 0.415 | +3.75% | 3.63 | +0.83 | 0.115 |
| 3 | 0.406 | 1.5% | 3.6 | 0% | 0.113 |
| 4 | 0.398 | -0.5% | 3.57 | -0.83% | 0.111 |
| 5 | 0.390 | -2.5% | 3.56 | -1.1% | 0.110 |
| 6 | 0.384 | -4% | 3.52 | -2.2% | 0.109 |
| 7 | 0.370 | -7.5% | 3.48 | -3.3% | 0.106 |
| 8 | 0.360 | -10% | 3.46 | -3.9% | 0.104 |
| 9 | 0.348 | -13% | 3.44 | -4.4% | 0.101 |
| 10 | 0.335 | -16.25% | 3.41 | -5.3% | 0.098 |

Fig. 4

| t | $V_1$ (ml) | $\delta V_1$ | $V_2$ (ml) | $\delta V_2$ | $V_1/V_2$ |
|---|---|---|---|---|---|
| 0 | 0.44 | +10% | 3.68 | +2.2% | 0.121 |
| 1 | 0.426 | +6.5% | 3.65 | +1.4% | 0.117 |
| 2 | 0.415 | 3.75% | 3.63 | +0.83 | 0.115 |
| 3 | 0.396 | -1% | 3.6 | 0% | 0.11 |
| 4 | 0.378 | -5.5% | 3.57 | -0.83% | 0.106 |
| 5 | 0.367 | -8.25% | 3.56 | -1.1% | 0.103 |
| 6 | 0.350 | -12.5% | 3.56 | -1.1% | 0.098 |
| 7 | 0.324 | -19% | 3.54 | -1.7% | 0.092 |
| 8 | 0.310 | -22.5% | 3.5 | -2.8% | 0.089 |
| 9 | 0.285 | -28.75% | 3.5 | -2.8% | 0.081 |
| 10 | 0.268 | -33% | 3.47 | -3.6% | 0.077 |

Fig. 5

PLASTIC TEST TUBE FOR TAKING BLOOD SAMPLES

TECHNICAL FIELD

The present invention relates to a plastic test tube for taking blood samples, intended to be used in particular in clinical tests for measuring the coagulation of a blood sample or in a test for measuring the erythrocyte sedimentation rate (ESR).

BACKGROUND OF THE INVENTION

During recent years, in the test-tube manufacturing sector, glass has been gradually abandoned and there has been an increasing use of plastic polymers such as, for example, polyethylene terephthalate (PET), polypropylene (PP), polyethylene (PE), polyvinyl chloride (PVC), polyurethane (PUR), polystyrene (PS) or olefin and ethylene-vinyl alcohol (EVOH) copolymers.

Compared to glass, materials such as PET, PP or PE offer undoubted advantages from a processing point of view and from the point of view of the mechanical properties which are imparted to the test tubes.

Test tubes made with these materials are in fact lighter, more resistant to impacts and, in particular, less costly than glass test tubes, since, owing to the greater ease of using injection moulding techniques, the production time and costs may be reduced considerably.

In general, test tubes for taking blood samples must be able to maintain, for a predetermined minimum life span, a well-defined blood intake capacity by ensuring that there is a certain degree of vacuum still present in the test tube compared to the vacuum pre-set at the time of sealing thereof. This capacity is measured in the form of the intake blood volume and corresponds to a fraction of the nominal volume V of the test tube. This fraction will be referred to below as the intake vacuum volume $V2$. The duration of the life span of a test tube is closely linked to the permeability of the walls of the said test tube and therefore the gas barrier properties of the materials used.

As is known, test tubes for taking blood samples which are specifically intended for clinical tests for measurement of the coagulation or for measuring the erythrocyte sedimentation rate (ESR) contain inside them a predetermined quantity of an anti-coagulating substance (usually an aqueous solution of sodium citrate) which at the time when the blood sample is taken is mixed with the blood, preventing coagulation thereof, and therefore allows the examination to be carried out at a later time. For the coagulation test it is at present envisaged that the anti-coagulating solution is mixed with the blood in a volumetric ratio of about 1:9 (=0.111), while for measurement of the ESR it is currently envisaged that the anti-coagulating solution is mixed with the blood in a ratio of about 1:4 (=0.25).

Operationally speaking, the inside of the test tubes intended for these tests must therefore usually have a ratio $V1/V2$ of about 1:9 or about 1:4 between the volume of anti-coagulating solution $V1$ and the intake vacuum volume $V2$. The sum of the intake vacuum volume $V2$ and the anti-coagulant volume $V1$ defines the working volume Vu of the test tube which is established a priori by the manufacturer. The working volume Vu, which in most cases is fixed between 1.5 and 4.5 ml, occupies only a fraction of the nominal volume V of the said test tube, while the remaining fraction, defined as the mixing volume Vm, is left free to allow mixing of the blood with the anti-coagulant.

Obviously, in order to achieve the volumetric ratio of 1:9, the anti-coagulant volume and the intake vacuum volume must occupy $\frac{1}{10}$th and $\frac{9}{10}$ths, respectively, of the working volume Vu, whereas in order to achieve the ratio of 1:4 they must occupy $\frac{1}{5}$th and $\frac{4}{5}$ths of the working volume, respectively.

In order for the abovementioned volumetric ratios to be kept within clinically acceptable limits, the test tubes must be able to ensure during the life span defined by the manufacturer that not only the intake vacuum volume, but also the anti-coagulant solution volume are maintained. Therefore, both the liquid (and vapour) barrier properties of the materials used for manufacture of the test tube and the gas barrier properties play a part when determining the life span of the test tube.

With regard to this specific point, the US standards as defined by the NCCLS (National Committee for Clinical Laboratory Standards), which are recognized internationally, fix a maximum tolerance of ±10% for variations, over time, of the vacuum volume $V2$ and the anti-coagulant volume $V1$ compared to the abovementioned ideal volumes. Corresponding deviations from the value of the ratio for anti-coagulant volume $V1$ and intake vacuum volume $V2$ are therefore permissible.

"Life span" of a test tube must therefore be understood as meaning the period of time for which a test tube manages to ensure variations in the intake vacuum volume and the anti-coagulant volume of less than ±10% of the abovementioned ideal volume values.

At present, the test tubes for the coagulation test or for erythrocyte sedimentation which are made of glass ensure life spans which are considerably longer than those instead ensured by plastic test tubes. In fact, glass test tubes are able to ensure a life span of more than one year compared to the few months of plastic test tubes. For example, in the case of a conventional glass test tube used for coagulation, the manufacturers may even guarantee a life span of 18 months, while, for a similar test tube made of PET with a wall thickness of about 0.9 mm, the manufacturers usually guarantee a maximum life span of 3 to 4 months. In the case of a PET test tube used for erythrocyte sedimentation, a life span of 5-6 months may also be reached.

It is known, in fact, that glass has both excellent gas and liquid barrier properties. At the moment, however, a plastic polymer which combines both these properties with the same efficiency as glass is not known.

Therefore, in a conventional test tube made of plastic, it is inevitable that within the space of a few months an incoming air flow A and outgoing water vapour flow B will be formed such as to cause the intake vacuum volume and the anti-coagulant volume to fall below the permitted limits.

These two flows are regulated by factors which are not yet entirely known and which are closely linked to the physical/chemical structure of the plastic polymers used for manufacture of the test tubes. In particular, in the case of test tubes made of PET, it is noted that the transmission of the vapour outside the test tubes is on average faster than the transmission of the air inside and this results in a more marked decrease in the anticoagulant volume over the vacuum volume.

The limited life spans which may be ensured for plastic tubes are, as already mentioned, in the region of a few months and greatly limit the commercial applicability of plastic test tubes. It should be remembered that on occasions transportation alone may take a few months, as when merchandise is shipped overseas, and that the storage time in warehouses may be prolonged for various reasons beyond the dates planned by the manufacturer. It may therefore happen that the test tubes are delivered to the end user close to the expiry date and therefore must be discarded should they not be used very soon after delivery.

In this connection it is therefore necessary to address the very urgent need in the plastic test tube manufacturing sector to improve the gas and liquid barrier properties of plastic vacuum test tubes in order to increase as far as possible their life spans.

European patent EP 571116 proposes solving this problem by covering externally the conventional plastic test tubes with a special adhesive film consisting of a polymer substrate and a very thin film of compounds based on silicon oxides. The gas and liquid barrier properties are provided mainly by the film of oxides which is deposited on the polymer substrate (formed for example by nylon, PVC, PP, PE, PCTFE or PET) using plasma deposition techniques.

A similar solution is also proposed in European patent EP 603717, which claims an outer, adhesive, protective film consisting of a polymer substrate (PP, PE or PET) and two very thin superimposed films, one of which is formed by a mixture of aluminium oxides and silicon and the other by an organic mixture comprising vinylidene chloride, acrylonitrile, methyl methacrylate, methacrylate and/or acrylic acid copolymers.

The European patents EP 735921 and EP 1175941 solve the problem by combining test tubes one inside the other one, the inner one being made with a polymer material having liquid barrier properties (for example PP) and the outer one being made with a polymer material having gas barrier properties (for example PET).

The abovementioned solutions of the prior art, while solving substantially the problem of the excessive gas and liquid permeability of plastic test tubes, introduce however into the production processes plant- and management-related problems which are often considerable and result in an increase in the production times and costs.

For example, the solutions described in the patents EP 571116 and EP 603717 require the purchase of costly oxide-coated films, while the solutions described in the patents EP 735921 and EP 1175941 require at least diversification of the test tube production lines (for inner test tubes and outer test tubes) and the provision of a final assembly line.

SUMMARY OF THE INVENTION

In this situation, therefore, the object of the present invention is to propose a solution which is an alternative to the solutions of the prior art mentioned above, by providing a plastic test tube for taking blood samples, which ensures an increase in the minimum guaranteed life span and at the same is both low-cost and easy to manufacture.

These and other objects are all achieved by a plastic test tube for taking blood samples under a vacuum in accordance with the accompanying claims.

BRIEF DESCRIPTION OF THE DRAWINGS

The technical features of the invention in accordance with the abovementioned objects may be clearly determined from the contents of the claims provided below and the advantages thereof will emerge more clearly from the detailed description which follows, provided with reference to the accompanying drawings, which show a purely exemplary and non-limiting embodiment thereof, in which:

FIG. 4 shows the details relating to variation, over time, in the vacuum volume and the anti-coagulant volume of a test tube according to the invention;

FIG. 5 shows the data relating to variation, over time, in the vacuum volume and the anti-coagulant volume of a conventional test tube;

DETAILED DESCRIPTION OF THE INVENTION

With reference to the accompanying drawings 1 denotes in its entirety a test tube for taking blood samples according to the present invention.

In particular, the abovementioned test tube 1 may be used in clinical tests for evaluating the coagulation of a blood sample or in a test for measuring the erythrocyte sedimentation rate (ESR).

Figure 1A:
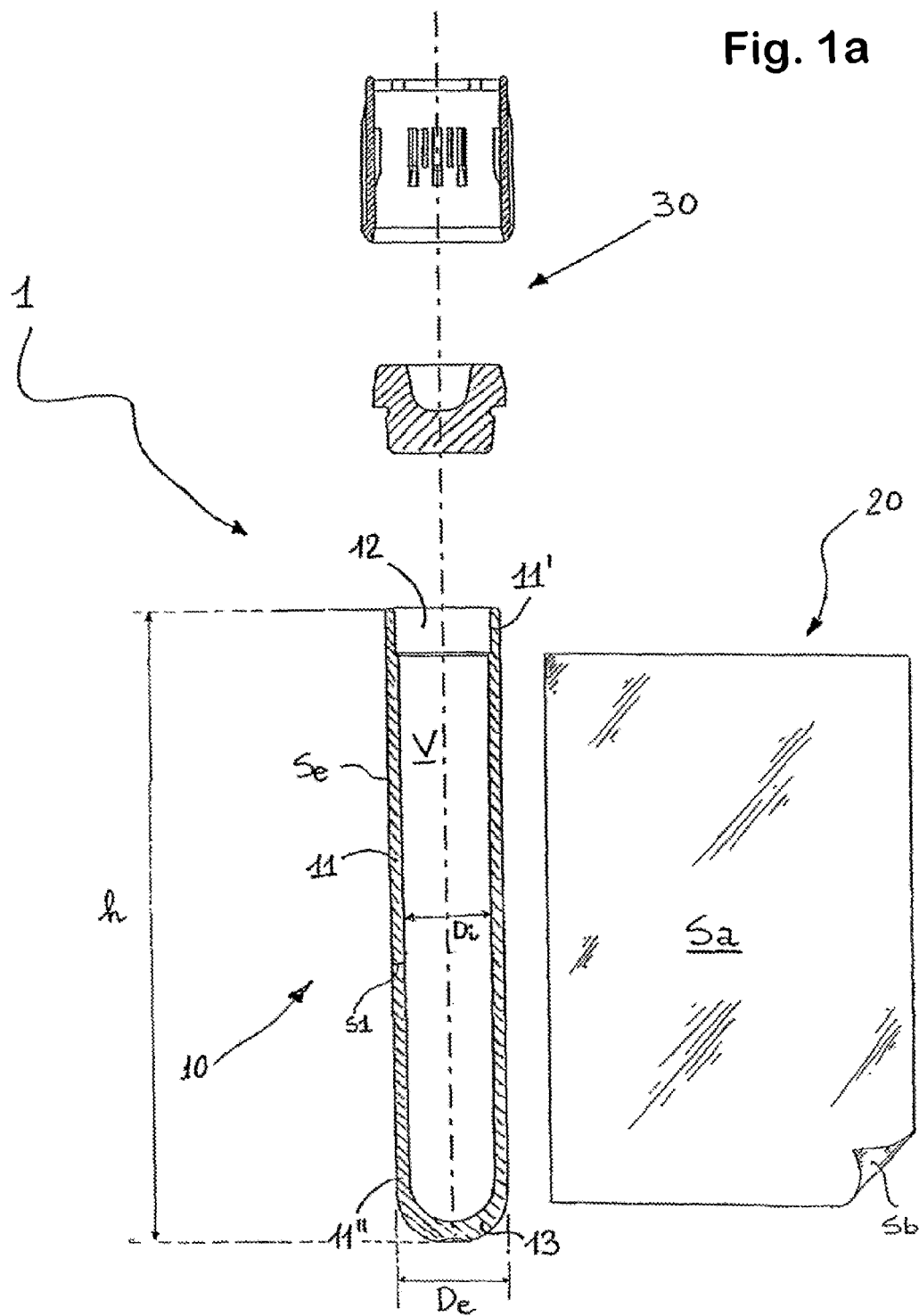
FIG. 1a shows an exploded view of the test tube according to the invention.
Figure 1B:
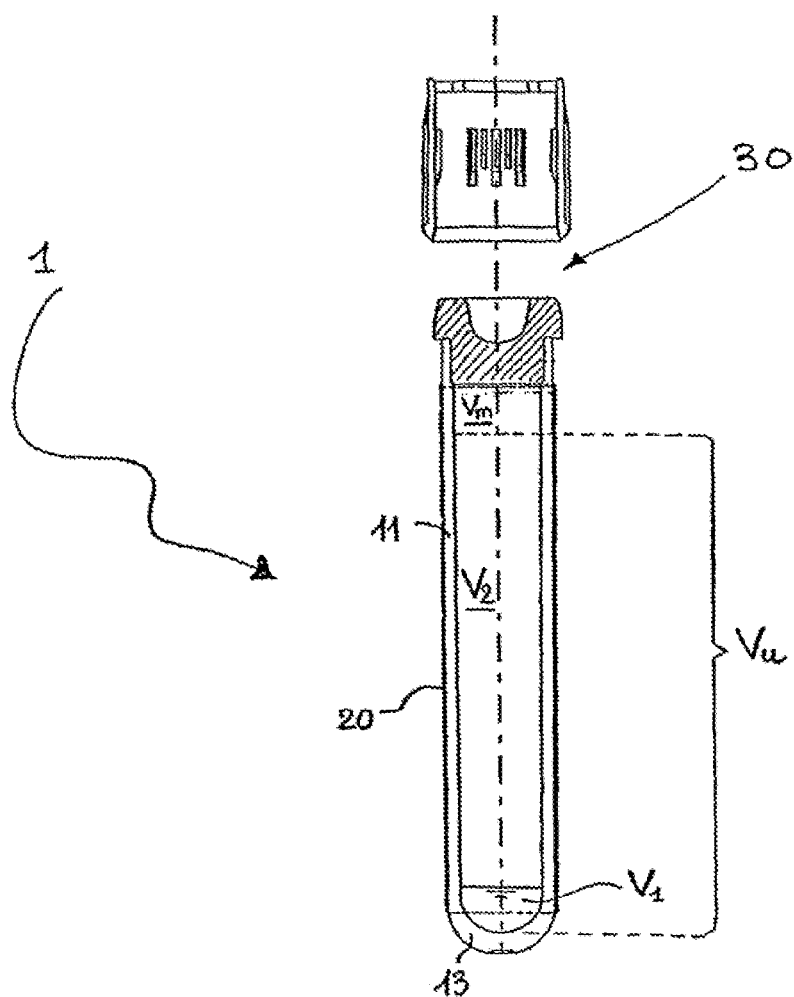
FIG. 1b shows a cross-sectional view of the test tube according to the invention in the assembled condition.
Figure 1C:
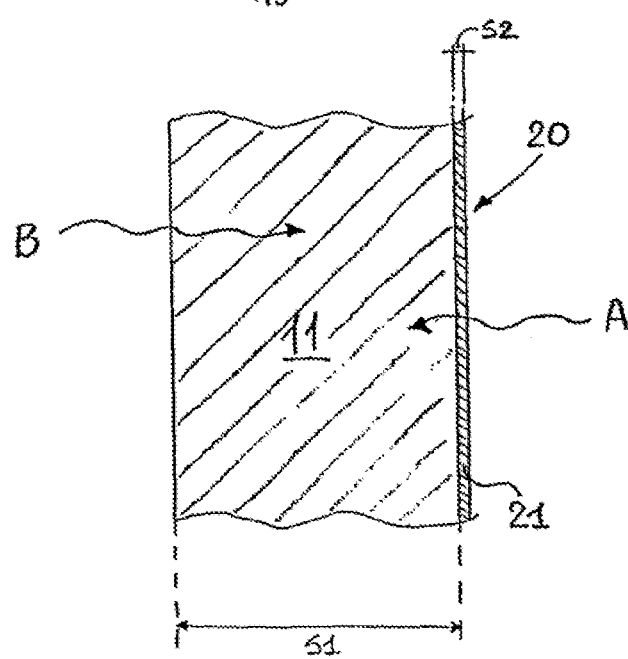
FIG. 1c shows a cross-sectional view of a detail of the test tube according to the invention relating to the combined arrangement of a tubular body and a protective film.

As can be seen in FIGS. 1a and 1b, the test tube 1 comprises a hollow tubular body 10, an adhesive protective film 20 to be applied externally onto the tubular body 10 and a stopper 30 to be arranged so as to close the tubular body 10.

In greater detail, the tubular body 10 is made of polyethylene terephthalate (PET) so as to form a gas barrier and has a tubular containing wall 11 which defines an outer surface Se to which the abovementioned protective film 20 adheres. At a first end 11' of the abovementioned wall 11, the tubular body 10 has an open mouth for insertion of liquids on which the abovementioned stopper 30 acts so as to provide a hermetic closure. At a second end 11' of the wall 11, opposite to the first end, the tubular body 10 has a closed bottom 13 which is preferably rounded.

As can be seen in particular in FIG. 1a, the tubular body 10 is tapered from the mouth 12 towards the closed bottom 13 and its wall 11 has a thickness s1 which is not constant and which varies from a minimum in the vicinity of the mouth 12 to a maximum in the vicinity of the bottom 13. In the remainder of the description, the thickness s1 of the wall 1 is understood as being the mean thickness of the wall 11 calculated between bottom and mouth, as will be explained more fully further below.

The outer mean thickness De of the tubular body 10 is set at about 12-13 mm depending on the present standards (dimensions of the needle holder, centrifuging chambers, etc.), although larger or smaller diameters may be envisaged.

The height h of the test tube 1 varies depending on the uses for which the test tube 1 is intended and is preferably between 70-80 mm.

The nominal volume V of the test tube 1 is defined by the inner mean diameter Di and by the height h and is divided into working volume Vu and mixing volume Vm. Preferably, the working volume Vu is fixed within the range of 1.5 ml to 4.5 ml, although it is possible to envisage test tubes with working volumes Vu outside of the range mentioned.

From a functional point of view, the test tube 1 is able to contain a predefined volume of an aqueous anticoagulant solution V1 (preferably sodium citrate in an amount equal to 3.8% or 3.2%), occupying a fraction of the working volume Vu, and an intake vacuum volume V2, occupying the remaining fraction of the working volume Vu.

If the test tube 1 is intended to be used in tests for evaluating the coagulation of a blood sample, ideally the volume of anti-coagulant V1 occupies 1/10th of the working volume Vu, while the intake vacuum volume V2 occupies 9/10ths of the working volume Vu so as to achieve the volumetric ratio of 1:9 (=0.111). At the time of sealing it is possible to introduce 10% more of anti-coagulant volume or vacuum volume.

If the test tube 1 is intended to be used in a test for measuring the ESR of a blood sample, ideally the anti-coagulant volume V1 occupies 1/5th of the working volume Vu, while the intake vacuum volume V2 occupies 4/5ths of the working volume Vu in order to ensure the volumetric ratio of 1:4 (=0.25). In this case also, at the moment of sealing, it is possible to introduce 10% more of anti-coagulant volume or vacuum volume.

According to the invention, the wall 11 of the tubular body 10 has a thickness s1 in the range of 1 mm to 3 mm; the protective film 20 is defined by a layer 21 of polypropylene (PP), polyethylene (PE) or copolymers thereof, so as to form a liquid barrier; the layer 21 has a thickness s2 in the range of 40 µm to 60 µm.

It has been established that the wall 11 and the layer 21, with thicknesses s1 and s2, respectively, within the above-mentioned ranges, produce a combined gas and liquid barrier action which increases surprisingly the life span of the test tube 1 compared to conventional test tubes. This combined barrier effect allows the incoming air flow A and outgoing vapour flow B to be kept on average proportional, regulating in particular the speed of transmission of the vapour from the inside to the outside. This has been confirmed by trial tests carried out on test tubes according to the invention and on conventional test tubes. These results are shown partly in FIGS. 4 and 5 and in FIGS. 2 and 3 and are commented upon in the example given at the end of the description.

More particularly, it has been determined that, in test tubes 1 according to the invention used for tests for measuring the ESR, the combined effect of the wall 11 and the layer 21 keeps, for a period of time of at least 12 months, the variation in the vacuum volume V2 within the range defined by ±10% of 4/5ths of the working volume Vu and the variations in anti-coagulant volume V1 within the range defined by ±10% of 1/5th of the internal volume V.

It has been also been established that in test tubes 1 according to the invention used for the coagulation test the combined effect of the wall 11 and the layer 21 keep, for a period of time of at least 8 months, the variations in the vacuum volume V2 within the range defined by ±10% of 9/10ths of the working volume Vu and the variations in the anti-coagulant volume V1 within the range defined by ±10% of 1/10th of the working volume V.

From a production point of view, the test tube 1 according to the invention does not require any substantial modification to the production lines used for test tubes of the conventional type. The application of the protective film 20 onto the tubular body 10 may also be performed by means of the apparatus which are normally envisaged for applying paper labels onto conventional test tubes. It must be pointed out, moreover, that a protective film made of PP, PE or copolymers in accordance with that envisaged by the invention is certainly less costly than an oxide-coated film protective film, to the benefit of the final cost of the test tube 1.

In accordance with a preferred embodiment of the present invention, the layer 21 of protective film 20 is formed by bioriented polypropylene with a density in the range of 32 to 64 $g/m^2$.

The protective film 20 is provided on one side with an adhesive surface Sb which comes into contact with the outer surface Se of the tubular body. This adhesive surface Sb is formed by a very thin film of glue based preferably on natural rubber and acrylic compounds. This type of glue has a low solvent content. This reduces considerably the possibility that the blood sample taken may be contaminated as a result of permeation of the solvents through the PET wall.

On the opposite side, namely the side directed towards the outside, the protective film 20 has an outer surface Sa which can be written on such that it is able to act as a marking label for the test tube 1.

In accordance with the constructional embodiment shown in FIGS. 1a and 1b, the protective film 20 has a rectangular shape and has a size such as to cover the (substantially cylindrical) outer surface Se of the tubular body 10. In any case it is possible to shape the protective film 20 in such a way as to line also the bottom 13 of the test tube and thus slow down the transmission of air and vapour also in this portion of the test tube.

Example

A comparison was performed between a test tube according to the invention and a conventional test tube, assessing gravimetrically over a period of 10 months the respective variations in the volume of anti-coagulant solution V1 (sodium citrate 3.8%) and the intake vacuum volume V2. Both the test tubes are of the type intended for a coagulation test, are made of PET and have a working volume of 4 ml. The conventional test tube has a wall thickness of 0.9 mm. The test tube according to the invention has a wall thickness s1 of 1 mm and is lined with a protective film of bioriented PP with a density of 49 $g/m^2$ and thickness s2 of 52 µm.

Both the test tubes have been sealed with an anti-coagulant volume V1 10% greater than the ideal volume of 1/10th of the working volume Vu, namely 440 µl (0.44 ml) of solution instead of 400 µl (0.40 ml) were introduced. The intake vacuum volume V2 was increased by about 2.22% with respect to the ideal value of 9/10ths of the working volume Vu, namely the volume V2 was equal to 3.68 ml instead of 3.60 ml.

The results of the tests on the test tube according to the invention, indicated by the letter A, are shown in FIG. 4, while the results of the tests on the conventional test tube, indicated by the letter B, are shown in FIG. 5. The time t is measured in months, while the variations δV1 and δV2, without reference to dimensions, are calculated with respect to the ideal values which are 400 µl (0.40 ml) for V1 and 3.60 ml for V2.

For a more immediate visual comparison, the trend of the volume of anti-coagulant V1 both for the test tube according to the invention (indicated by A) and for the conventional test tube (indicated by B) has been illustrated in a graph showing volume (µl) against time (where t is expressed in months). Similarly, in FIG. 3 the trend of the intake vacuum volume V2 both for the test tube according to the invention (indicated by A) and for the conventional test tube (indicated by B) has been illustrated in a graph showing volume (ml) against time (expressed in months).

On the basis of the NCCLS standards the acceptability threshold for the value of the anticoagulant volume V1 is 360 µl (0.36 ml), while for the intake vacuum volume V2 the threshold is 3.24 ml.

Figure 2:
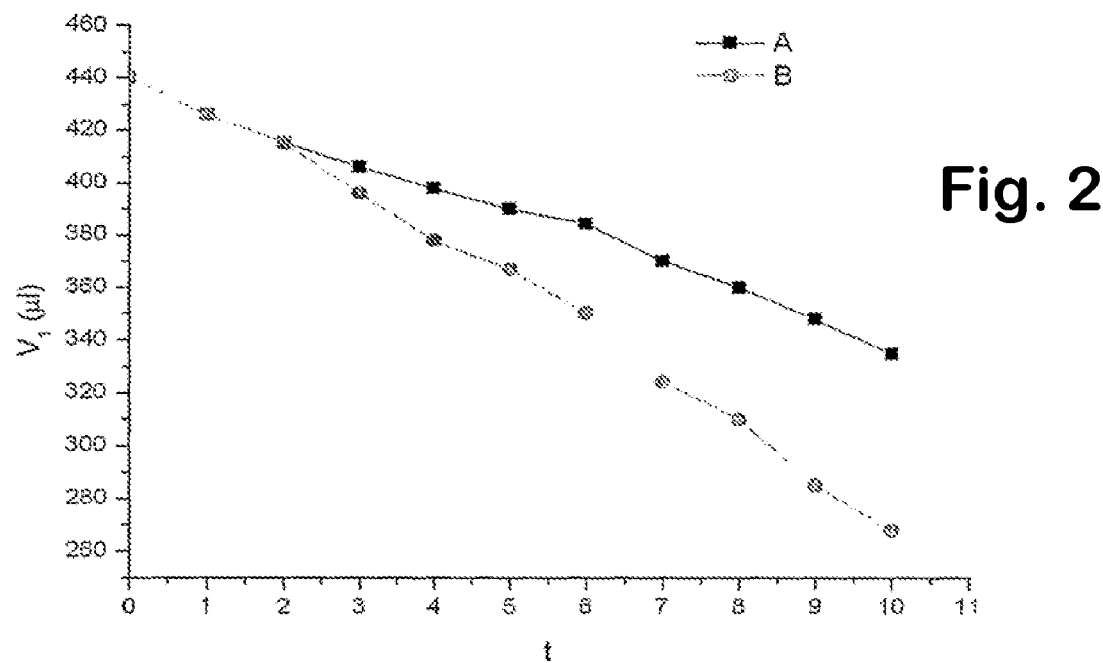
FIG. 2 shows, in a volume/time graph, a comparison between the trend, over time, of the anti-coagulant volume in a conventional test tube and in a test tube according to the invention on the basis of the data shown in Tables 1 and 2.

As can be seen from the FIGS. 4 and 5 and from FIG. 2, in the test tube according to the invention (A) the anti-coagulant volume V1 remains within the acceptability threshold up to the 8th month, while in the conventional test tube (B) the anti-coagulant volume V1 exceeds the threshold already between the 5th and 6th month. In both the test tubes, on the other hand, the intake vacuum volume V1 remains above the corresponding acceptability threshold well beyond the 10th month.

The test tube according to the invention therefore guarantees a life span which is at least 8 months and therefore longer than that of a conventional test tube.

Figure 3:
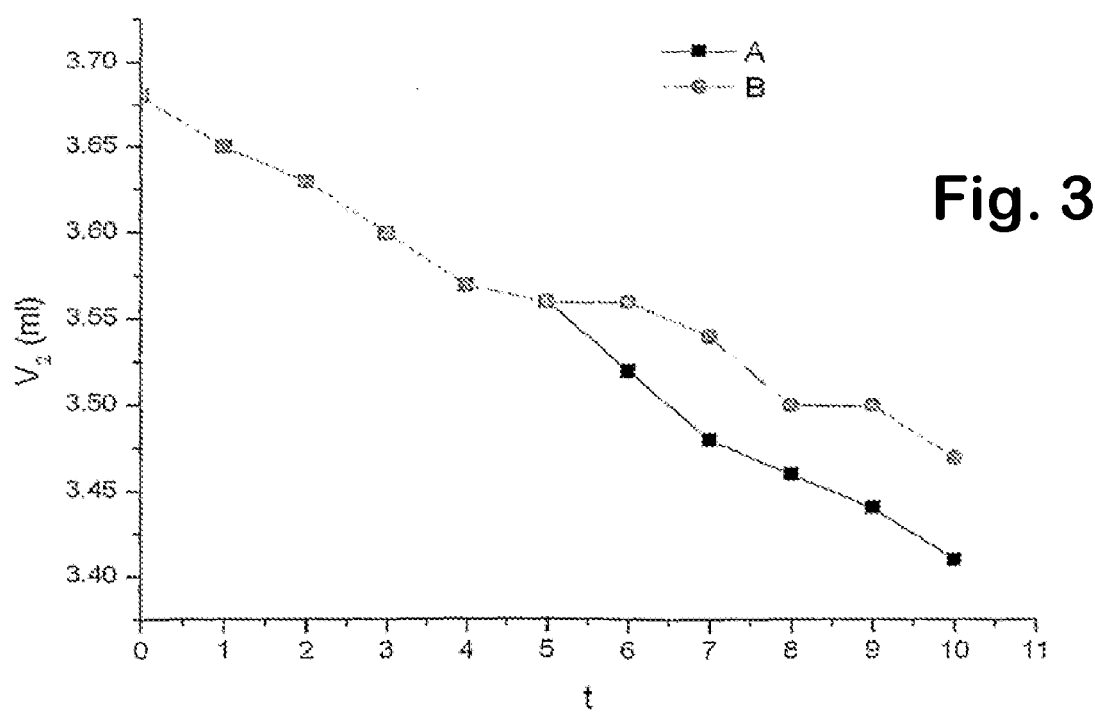
FIG. 3 shows, in a volume/time graph, a comparison between the trend, over time, of the vacuum volume in a conventional test tube and in a test tube according to the invention on the basis of the data shown in Tables 1 and 2.

As can be visually understood from the graphs shown in FIGS. 2 and 3, during the first months the values of the vacuum volume V2 and anti-coagulant volume V1 of the two test tubes coincide. This is due to the absorption of air and vapour by the PET wall; this phenomenon is the precursor to the formation of continuous flows of matter through the wall. Obviously this phenomenon is the same for both the test tubes.

In the graph according to FIG. 3 it can be seen how the variation in the intake vacuum volume is more marked in the test tube according to the invention than in the conventional test tube. This is due to the fact that the greater loss of anti-coagulant volume in the conventional test tube compensates partly for the decrease in the vacuum volume. In reality this does not constitute an advantage in that in the conventional test tube the ratio V1/V2 diverges more, over time, from the ideal value than instead occurs with the test tube according to the invention.

In the test tube according to the invention it can be noted that the ratio V1/V2 remains closer to the ideal value by way of confirmation of the fact that the test tube according to the invention allows the incoming air flow A and the outgoing vapour flow B to be kept on average more proportional.

During other trial tests (not described here) life spans of at least 8 months for test tubes according to the invention with a thickness s1 of the wall 11 in the range of 1.0 to 1.2 mm and a thickness s2 of the layer 21 in the range of 50 to 54 μm were also observed.

In the case of test tubes according to the invention with a thickness s1 of the wall 11 in the range 1.3 to 1.6 mm and a thickness s2 of the layer 21 in the range of 50 to 54 μm, life spans of at least 10 months were observed.

Moreover, in the case of test tubes according to the invention with a thickness s1 of the wall 11 in the range of 1.7 to 3 mm and a thickness s2 of the layer 21 in the range of 50 to 54 μm, life spans of at least 12 months were observed.

The invention thus conceived therefore achieves the predefined objects.

Obviously, it may also assume, in its practical embodiment, forms and configurations different from that illustrated above without thereby departing from the present scope of the invention.

Moreover, all the details may be replaced by technically equivalent parts, and the dimensions, forms and materials used may be of any nature according to requirements.

What is claimed is:

1. Plastic test tube for taking blood samples, comprising:
   a hollow tubular body made of polyethylene terephthalate and having: a tubular wall which delimits a working volume and defines an outer surface; an open mouth for insertion of liquids at a first end of said wall; and a bottom for closing a second end of said wall; and
   an adhesive protective film able to adhere to the wall of said tubular body over at least a portion of said outer surface;
   wherein the wall of said tubular body has a thickness in the range of 1 to 3 mm and said protective film is defined by a layer of polypropylene, polyethylene or copolymers thereof, which has a thickness in the range of 40 to 60 μm and is able to form a liquid barrier.

2. Test tube according to claim 1, in particular to be used in tests for evaluation of the ESR, comprising:
   a stopper arranged so as to close said mouth;
   a predefined volume of an aqueous anti-coagulant solution which is substantially equivalent to ⅕th of said working volume and inserted inside said tubular body;
   an intake vacuum volume substantially equivalent to ⅘ths of said working volume;
   said wall and said layer providing a combined gas and liquid barrier action which keeps for a period of at least 12 months the variations in said intake vacuum volume within the range defined by ±10% of ⅘ths of said working volume and the variations in said volume of anti-coagulant within the range defined by ±10% of ⅕th of said working volume.

3. Test tube according to claim 1, in particular to be used in coagulation evaluation tests, comprising:
   a stopper arranged so as to close said mouth;
   a volume of an aqueous anti-coagulant solution which is substantially equivalent to ¹⁄₁₀th of said working volume and inserted inside said tubular body;
   an intake vacuum volume substantially equivalent to ⁹⁄₁₀ths of said working volume;
   said wall and said layer providing a combined gas and liquid barrier action which keeps for a period of at least 8 months the variations in said intake vacuum volume within the range defined by ±10% of ⁹⁄₁₀ths of said working volume and the variations in said anti-coagulant volume within the range defined by ±10% of ¹⁄₁₀th of said working volume.

4. Test tube according to claim 3, in which the thickness of said wall is within the range of 1.0 to 1.2 mm and the thickness of said layer is within the range of 50 to 54 μm, said test tube thereby keeping for a period of at least 8 months the variations in said intake vacuum volume within a range of ±10% of ¹⁄₁₀th of said working volume and the variations in said anti-coagulant volume within a range of ±10% of ⁹⁄₁₀ths of said working volume.

5. Test tube according to claim 3, in which the thickness of said wall is within the range of 1.3 to 1.6 mm and the thickness of said layer is within the range of 50 to 54 μm, said test tube thereby keeping for a period of at least 10 months the variations in said intake vacuum volume within a range of ±10% of ¹⁄₁₀th of said working volume and the variations in said anti-coagulant volume within a range of ±10% of ⁹⁄₁₀ths of said working volume.

6. Test tube according to claim 3, in which the thickness of said wall is within the range of 1.7 to 3 mm and the thickness of said layer is within the range of 50 to 54 μm, said test tube thereby keeping for a period of at least 12 months the variations in said intake vacuum volume within a range of ±10% of ¹⁄₁₀th of said working volume and the variations in said anti-coagulant volume within a range of ±10% of ⁹⁄₁₀ths of said working volume.

7. Test tube according to any of claims 1 to 6 in which the layer of said protective film is formed by bioriented polypropylene with a density in the range of 32 to 64 g/m².

8. Test tube according to any of claims 1 to 6 in which said protective film also extends to the outer surface of said bottom.

9. Test tube according to any of claims 1 to 6 in which said protective film has an outer surface which can be written on and which acts as a marking label for said test tube.

10. Test tube according to any of claims 1 to 6 in which said protective film has an adhesive formed by a film of glue based on natural rubber and acrylic compounds.

* * * * *